US005693516A

United States Patent [19]

Blinkovsky

[11] Patent Number: 5,693,516
[45] Date of Patent: Dec. 2, 1997

[54] METHOD FOR SOLUBILIZING PROTEINS IN ORGANIC SOLVENTS

[75] Inventor: Alexander Blinkovsky, Davis, Calif.

[73] Assignee: Novo Nordisk Biotech, Inc., Davis, Calif.

[21] Appl. No.: 562,536

[22] Filed: Nov. 27, 1995

[51] Int. Cl.$^6$ .................................................. C12N 9/96
[52] U.S. Cl. ............................ 435/188; 530/402; 530/422
[58] Field of Search ............................ 435/188; 530/402, 530/422

[56] References Cited

FOREIGN PATENT DOCUMENTS 6-303973  4/1993  Japan .

OTHER PUBLICATIONS

Paradkar et al., J. Am. Chem. Soc., vol. 116, No. 11, pp. 5009–5010, 1994.
Basheer et al., Biotechnology & Bioenginnering, vol. 45, pp. 187–195, 1995.
Okahat et al., The Chem. Society of Japan, vol. 65, pp. 2411–2420, 1992.
Bromberg et al., Applied Biological Sciences, vol. 92, pp. 1262–1266, 1995.
Bromberg et al., Applied Biological Sciences, vol. 91, pp. 143–147, 1994.

*Primary Examiner*—Leon B. Lankford, Jr.
*Attorney, Agent, or Firm*—Steve T. Zelson, Esq.; Valeta A. Gregg, Esq.

[57] ABSTRACT

The present invention relates to a method for producing a protein composition soluble in organic solvents, comprising mixing a protein of interest with a surfactant and a water immiscible organic solvent in amounts and under conditions conducive to the formation of a reverse micelle solution, and evaporating the resulting reverse micelle solution to dryness.

29 Claims, No Drawings

METHOD FOR SOLUBILIZING PROTEINS IN ORGANIC SOLVENTS

FIELD OF THE INVENTION

The present invention relates to a method for preparing protein compositions which are soluble in a variety of organic solvents.

BACKGROUND OF THE INVENTION

Although many proteins have found widespread use in a variety of industrial processes, as well as health care applications, the full commercial potential of certain proteins cannot be realized because of limitations in their ability to dissolve in and/or be transported through nonaqueous media. Considerable research efforts have recently focused on developing methodology which will permit solubilization of a protein in organic solvents without significant loss of its useful biological properties. Such a property is important, for example, to enhance bioavailability of proteins by permitting their crossing of cellular membranes, skin, intestinal mucosa, etc. This property can also be important in industrial settings in which catalytic reactions are required or desirable in a non-aqueous environment, for example in organic synthesis or the dry cleaning or textile industries.

Many different approaches have been taken to attempt to achieve this goal. Some of these approaches include chemical modification of the enzyme e.g., by attachment of PEG or hydrophobic residues, immobilization, and complexing or coating with surfactants,. Although many different systems have been described for this purpose(see, e.g., Paradkar and Dordick, J. Am. Chem. Soc. 116: 5009–5010, 1994; Basheer et al., Biotech. Bioeng. 45: 187–195, 1995; Bromberg and Klibanov, PNAS USA 92: 1262–1266, 1995; PNAS USA 91: 143–147, 1994; JP Laid Open Application No.6-303973). However, the known treatments result in compositions which are not highly soluble in organic solvents, or which can be used effectively with only a limited number or kinds of protein. Thus, although many such methods have been described and are available, no method has achieved widespread acceptance in the form of commercial application in the fields in which organic solvent-soluble proteins would be useful. The present invention now provides a method for preparing a protein composition which is readily and fully soluble, up to a level of nearly 100%, in a variety of organic solvents, and which provides such effective compositions with a wide variety of different types of proteins.

SUMMARY OF THE INVENTION

The present invention relates to a method for preparing a protein composition which is soluble in an organic solvent, the method comprising preparing a reverse micelle solution from a surfactant, a protein in aqueous solution, and a water immiscible organic solvent, and evaporating the solution to dryness. In a preferred embodiment, the surfactant is an ionic surfactant, more preferably an anionic surfactant. It is also preferred that in the solution, an amount of water is present which exceeds five molecules of water per molecule of surfactant. Upon drying of the reverse micelle-containing solution, the resulting protein composition is readily soluble in a variety of organic solvents at least to a level of 60% solubility, preferably at least 80% solubility, and most preferably at least 90%, and up to about 100% solubility. The invention also relates to the composition prepared by the method described above.

DETAILED DESCRIPTION OF THE INVENTION

In the method of the present invention, it is required that a reverse micelle system be formed by the protein, an organic solvent, water and a surfactant. As used in the present specification and claims, the term "reverse micelles solution" is defined as a water-in-oil microemulsion comprising droplets having a size of between 0.0015–0.2 µm. This is distinguished from a reverse phase emulsion (see, for example Friberg, S. E. and Lindman, B., eds. Organizated Solutions, Marcel Dekker, NY, 1992). which is a water-in-oil emulsion (but not a microemulsion) which has a droplet size of 0.2–100 µm. These two categories are also distinguished by appearance (turbid for a reverse phase emulsion, transparent for a reverse micelle solution), and thermodynamic stability (unstable for a reverse phase emulsion, stable for a reverse micelle solution). A reverse phase emulsion will not provide the same results as a reverse micelle solution, as shown below in the examples.

Methods for making reverse micelle solutions are well known and widely reported in the scientific literature. See, for example, Luisi, P. L. and Straub, B., eds. Reverse Micelles, Plenum Press, NY, 1984; Martinek, K. et al., Biochim. Biophys. Acta 981.: 161–172, 1989; Luisi, P. L., Angew. Chem. Int. Ed. Engl. 24: 439–450, 1985. Any method known for production of reverse micelles in solution may be used in the present method.

The components for preparing the reverse micelles solution may vary. The choice of protein of course will always be variable. The reverse micelles solution is prepared in a water immiscible organic solvent. The water immiscible solvent is preferably an alkane, such as hexane, heptane, octane, isooctane, nonane, decane, undecane, dodecane, tridecane, tetradecane, pentadecane, hexadecane, heptadecane, or non-alkane, such as benzene, toluene, carbon tetrachloride, chloroform, hexanol, heptanol, octanol, 1-nonanol, 2-nonanol, 1-decanol, 2-decanol and the like or a mixture of them. In preparing the reverse micelles, the protein component is preferably in the form of an aqueous solution. More preferably, the protein is provided in the form of a buffered aqueous solution. The solution may be buffered with any standard buffering compound, and in one embodiment, the preferred buffer is a volatile salt. Such volatile salts include ammonium carbonate, ammonium bicarbonate, ammonium formate, ammonium acetate, ammonium propionate, ammonium sulfite or ammonium nitrite.

A surfactant is required to prepare reverse micelles. Any type of surfactant may be used in the present method, i.e., ionic(anionic or cationic) or nonionic. Examples of anionic surfactants are carboxylates, for example, a metal carboxylate of a long chain fatty acid; N-acylsarcosinates; mono- or diesters of phosphoric acid with fatty alcohol ethoxylates or salts of such esters; fatty alcohol sulphates such as sodium dodecyl sulphate, sodium octadecyl sulphate or sodium cetyl sulphate; ethoxylated fatty alcohol sulphates; ethoxylated alkylphenol sulphates; lignin sulphonates; petroleum sulphonates; alkyl aryl sulphonates such as alkyl-benzene sulphonates or lower alkylnaphthalene sulphonates, e.g., butylnaphthalene sulphonate; salts or sulphonated naphthaleneformaldehyde condensates; salts of sulphonated phenol-formaldehyde condensates; or more complex sulphonates such as amide sulphonates, e.g., the sulphonated condensation product of oleic acid and N-methyl taurine or the dialkyl sulphosuccinates, e.g., the sodium sulphonate or dioctyl succinate. A particularly preferred anionic surfactant is aerosol OT (sodium di(2-ethylhexyl)sulfosuccinate; AOT).

Examples of non-ionic surfactants are surfactants such as condensation products of fatty acid esters, fatty alcohols, fatty acid amides or fatty-alkyl- or alkenyl-substituted phenols with ethylene oxide, block copolymers of ethylene oxide and propylene oxide, acetylenic glycols such as 2,4,7,9-tetraethyl-5-decyn-4,7-diol, or ethoxylated acetylenic glycols.

Examples of cationic surfactants are surfactants such as aliphatic mono-, di-, or polyamine as acetates, naphthenates or oleates; oxygen-containing amines such as an amine oxide of polyoxyethylene alkylamine; amide-linked amines prepared by the condensation of a carboxylic acid with a di- or polyamine; or quaternary ammonium salts.

The most preferred surfactants in the present method are anionic surfactants, and the most preferred surfactant for forming reverse micelles in the present method is AOT.

The components of the solution to prepare the reverse micelles are preferably present in specified proportions. For example, the typical solution will contain 70–99.5% (v/v) immiscible organic solvent, 0.2–30% (v/v) water, 0.5–20% (w/v) surfactant, and 0.05–5% (w/v) protein, although proportions will vary depending upon the nature of the organic solvent, surfactant and protein. A preferred composition is prepared from 1–4.5% (w/v) AOT, 90–99% (v/v) octane, 3–5% (v/v) water, and 0.05–0.5% (w/v) protein.

The transparent solution representing a reverse micelles system is then evaporated to dryness at temperature less than 37° C. This can be achieved by any method commonly used in the art for this purpose. The resulting product is a soaplike solid or viscous liquid, which can be used as is for dissolution in organic solvents and other nonaqueous media of interest. An additional advantageous aspect of this drying phase is that it serves to remove volatile salts, such as ammonium bicarbonate, ammonium acetate, and ammonium carbonate, if present as buffering agents in the aqueous solution containing the protein. This removal serves to render the resulting composition salt-free, but pH adjusted. Such properties are particularly useful in compositions intended for pharmaceutical use.

The composition of the present invention has many uses. One important application is in the administration of proteins for therapeutic purposes. As mentioned above, one of the major barriers to effective use of biologically active proteins is their inability to be effectively directed to the site where they are needed. Oral delivery is not an option for most proteins, but parenteral delivery of therapeutic proteins is hindered by the difficulty of transporting the protein across, for example, skin, gastrointestinal or nasal mucosa, or the blood-brain barrier, where lipids, in which proteins will not dissolve, provide a significant hurdle. The ability of the present compositions to dissolve in a nonaqueous solutions provides a convenient means for therapeutic protein delivery. Thus, the invention provides means for delivering such proteins as insulin, growth hormone(or any other peptide hormones), coagulation and anti-coagulation proteins, antibodies and the like.

The composition also provides an advantage for the dry cleaning industry. The use of enzymes for garment cleaning is widespread in laundry detergents, in which they can function in an aqueous environment. However, their use has not spread to dry cleaning because of the need to use an organic solvent.

Three organic solvents—perchloroethylene, 1,1,2-trichloro-1,2,2-trifluoroethane, and 1,1,1-trichloroethane—dominate the world market. In spite of their effectiveness, these three solvents pose environmental hazards due to the toxicity to the atmospheric ozone. The present compositions can be dissolved in a low toxicity dry cleaning solvent to permit enzyme-assisted cleaning and stain removal; such a combination has enhanced efficacy relative to the dry cleaning solvent alone, and further permits the use of a nontoxic, but perhaps less effective, solvent than those which are currently in use.

The compositions are also useful in organic syntheses, such as solid-phase peptide synthesis, textile modification, coal liquefaction, etc., in which enzymatic catalysis would be beneficial.

Finally, it will be recognized by those skilled in the art that although the present examples relate to the solubilization of proteins, other non-protein biologically active material which is not ordinarily soluble in lipids or other non-aqueous materials can also be effectively rendered soluble in an organic medium by the present method. Examples of such materials include vitamins, non-steroid pharmaceuticals and the like.

EXAMPLES

I. Solubilization of Lipase from *Thermomyces lanuginosus*.

300 µl of a lipase solution (90 mg/ml) in a $CH_3COONH_4$ buffer (50 mM, pH 7.0) are injected into 10 ml of a solution of sodium di (2-ethylhexyl) sulfosuccinate (AOT; 0.1M) in octane. Shaking (3–5 s) the emulsion results in the production of a reverse micelle system, as evidenced by a completely transparent and stable solution. The solution is initially dried at 33°–34° C. under reduced pressure in order to remove octane. The residue is dried overnight at 20°–22° C. under vacuum (150 millitor).

20.7 mg of the resulting composition are incubated in 1 ml of dry hexane (a water insoluble organic solvent) while stirring magnetically. A one minute incubation results in complete dissolution. The solution is centrifuged at 12,150 RCF. No precipitate is observed.

17.1 mg of the resulting composition are incubated in 1 ml of dry tetrahydrofuran (THF; a water soluble organic solvent) while stirring magnetically. A one minute incubation results in complete dissolution. The solution is centrifuged at 12,150 RCF. No precipitate is observed.

The lipase solution in hexane and in THF are examined for the presence of lipase. The method for determination of the lipase concentration is based on the hydrolysis of tributyrin by the enzyme and measurement of the alkali consumption in a automatic pH-titrator. To this end, aliquots of each solution are added to a tributyrin emulsion and velocity of the tributyrin hydrolysis is measured. Comparing the total lipase initial activity and the total lipase activity after the transfer into the organic solvents, it is found that the lipase is completely solubilized into both THF and hexane.

II. Solubilization of Laccase from Myceliophthora.

200 µl of a laccase solution (10 mg/ml) in a phosphate buffer (10 mM, pH 7.5) are injected into 8 ml of a solution of sodium di(2-ethylhexyl)sulfosuccinate (AOT; 0.1M) in octane. Shaking (3–5 s) the emulsion results in the production of a reverse micelle system, as evidenced by a completely transparent and stable solution. The solution is initially dried at 33°–34° C. under reduced pressure in order to remove octane. The residue is dried overnight at 20°–22° C. under vacuum (150 millitor). 15.6 mg of the resulting composition are incubated in 1 ml of dry hexane (a water insoluble organic solvent) while stirring magnetically. A one minute incubation results in complete dissolution. The solution is centrifuged at 12,150 RCF. No precipitate is observed.

17.9 mg of the resulting composition are incubated in 1 ml of dry tetrahydrofuran (THF; a water soluble organic solvent) while stirring magnetically. A one minute incubation results in complete dissolution. The solution is centrifuged at 12,150 RCF. No precipitate is observed.

The laccase solution in hexane and in THF are examined for the presence of laccase. The method for determination of the laccase concentration is based on the oxidation of catechol in a phosphate buffer (10 mM, pH7.5) by the enzyme and measurement of the optical absorbance at 420 nm in a spectrophotometer. To this end, aliquots of each solution are added to a catechol solution and initial velocity of the catechol oxidation is measured. Comparing the total laccase initial activity and the total laccase activity after the transfer into the organic solvents, it is found that the laccase is completely solubilized into both THF and hexane.

III. Comparison of Reverse Micelle Solution vs. Reverse Phase Emulsion

A. Solubilization of trypsin

1. According to the present method, 125 μl of a trypsin solution (38.8 mg/ml) in a $CH_3COONH_4$ buffer (10 mM, pH 7.0) are injected into 5 ml of a solution of AOT (0.1M) in octane. Shaking (3–5 s) the emulsion results in the production of a reverse micelle system, as evidenced by a completely transparent and stable solution. The solution is initially dried at 33°–34° C. under reduced pressure in order to remove octane. The residue is dried overnight at 20°–22° C. under vacuum (150 millitor).

20.7 mg of the resulting composition are incubated in 1 ml of dry hexane (a water insoluble organic solvent) while stirring magnetically. A one minute incubation results in complete dissolution. The solution is centrifuged at 12,150 RCF. No precipitate is observed. The spectrum of the solution against hexane shows the value of absorbance to be 0.849 $cm^{-1}$ at 280 nm.

20.1 mg of the resulting composition(hereinafter, the "A1" composition) are incubated in 1 ml of THF (a water soluble organic solvent) while stirring magnetically. A one minute incubation results in complete dissolution. The solution is centrifuged at 12,150 RCF. No precipitate is observed. The spectrum of the solution against THF shows the value of absorbance to 0.792 $cm^{-1}$ at 280 nm.

2. Utilizing the method disclosed in JP Application No. 6-303973, 125 μl of a trypsin solution (38.8 mg/ml) in a $CH_3COONH_4$ buffer (10 mM, pH 7.0) are diluted with 700 μl of water and then injected into 5 ml of AOT solution (0.1M) in octane. After shaking for three minutes, the emulsion does not result in a transparent solution, indicating that a reverse micelle system has not been formed. The emulsion is initially dried at 33°–34° C. on a rotovap in order to remove octane. The residue is dried overnight at 20°–22° C. under vacuum (150 millitorr).

90.7 mg of the resultant composition (hereinafter, the "A2" composition) are incubated in 1 ml of dry hexane under magnetic stirring. A one hour incubation results in an opaque solution. This solution is centrifuged at 12,150 RCF; centrifugation leads to phase separation. A white precipitate and an absolutely transparent supernatant are observed. The spectrum of the supernatant against hexane shows the value of absorbance as 0.421 $cm^{-1}$ at 280 nm. The spectra of the solution described above in A1, and of the supernatant of A2 in hexane are very similar. This shows that the method described in Example A1 above provides a solubility of about 100% of the trypsin in dry hexane, but the method of Example A2 solubilizes only about 49.6% of the trypsin ($A_{280}$ 0.421/$A_{280}$ 0.849=0.496).

20.1 mg of the resulting A2 composition are incubated in 1 ml of THF while stirring magnetically. A one hour incubation results in an opaque solution. The solution is centrifuged at 12,150 RCF. Centrifugation leads again to phase separation. The spectrum of the supernatant against THF shows the value of absorbance to be 0.425 $cm^{-1}$ at 280nm. The spectra of the solution from A1 and A2 in THF is very similar. In this case, it is shown that the A1 method provides solubility of 100% of trypsin in THF, but the A2 method permits solubilization of only 53.7% of the trypsin($A_{280}$ 0.425/$A_{280}$ 0.792=0.537)

Thus, the trypsin-containing composition produced by the present method is more readily soluble in both a water-immiscible and a water-miscible organic solvent.

B. Solubilization of cytochrome C 1. 150 μl of a cytochrome C solution(21.3 mg/ml) in a $CH_3COONH_4$ buffer (50 mM, pH 7.0) are injected into 10 ml of an AOT solution (0.1M) in octane. The shaking (3–5 s) of the emulsion results in the reverse micelle system, as demonstrated by the production of a completely transparent and stable red solution. This solution is initially dried at 33°–34° C. on a rotovap in order to remove octane. The residue is dried overnight at 20°–22° C. under vacuum (150 millitorr).

10.5 mg of the resulting composition are incubated in 1 ml of dry hexane while stirring magnetically. A 1 minute incubation results in the transparent solution. However, the centrifugation at 12,150 RCF leads to a very small amount of the precipitate and a transparent red supernatant. It is later determined that 85% of the cytochrome C in the organic (hexane)phase. The value of absorbance is found to be 0.512 $cm^{-1}$ at 410 nm(the characteristic wavelength). Using the method substantially as described above in A1, the AOT/cytochrome complex is found to highly soluble in THF as well.

2. 500 μl of cytochrome C solution (5.4 mg/ml) in the phosphate buffer (50 mM, pH 7.0) are injected into 5 ml of the AOT solution (0.05M) in octane. Shaking for three minutes, and magnetic stirring for ten minutes does not result in a transparent system. The emulsion is initially dried at 33°–34° C. on a rotovap in order to remove octane. The residue is dried overnight at 20°–22° C. under vacuum (150 millitorr).

11.1 mg of the resulting are incubated in 1 ml of dry hexane while stirring magnetically. A one hour incubation results in a turbid system. This suspension is centrifuged at 12,150 RCF. Centrifugation results in a red precipitate and colorless transparent supernatant. The absorbance spectrum of the supernatant against hexane confirms the absence of cytochrome C in the hexane phase. The value of absorbance at 410 nm is found to be 0.01 $cm^{-1}$. This AOT/cytochrome composition is also found to be almost completely insoluble in THF ($A_{410}$=0.01 $cm^{-1}$).

Thus, with cytochrome C, the present method is shown to be superior in producing a composition which is highly soluble in different types of organic solvents.

What is claimed is:

1. A method for producing a protein composition soluble in organic solvents, comprising:
    (a) forming an aqueous solution of a protein of interest;
    (b) mixing the aqueous protein solution of step (a) with a solution comprising a surfactant in a water immiscible organic solvent, wherein a reverse micelle solution is formed, and
    (c) evaporating the reverse micelle solution of step (b) to dryness, wherein the resulting protein composition is soluble in both water miscible and water immiscible organic solvents.

2. The method to claim 1, wherein the aqueous solution is buffered.

3. The method according to claim 2 which is buffered with a volatile salt selected from the group consisting of ammonium carbonate, ammonium bicarbonate, and ammonium acetate.

4. The method of claim 1, wherein the organic solvent is an alkane.

5. The method of claim 1 wherein the surfactant is an ionic surfactant.

6. The method of claim 1, wherein the surfactant is an avionic surfactant.

7. The method of claim 6 in which the surfactant is AOT.

8. The method of claim 1, wherein the protein is an enzyme.

9. The method of claim 3 in which volatile salts are removed during drying.

10. A protein composition soluble in organic solvents prepared according to a method comprising mixing an aqueous solution of a protein of interest with a solution comprising a surfactant in a water immiscible organic solvent in amounts and under conditions conducive to the formation of a reverse micelle solution, and evaporating the resulting reverse micelle solution to dryness, wherein the resulting protein composition is soluble in water miscible and water immiscible organic solvents.

11. The composition of claim 10 which comprises an ionic surfactant.

12. The composition of claim 11 which comprises an anionic surfactant.

13. The composition of claim 12 which comprises AOT.

14. A protein composition soluble in organic solvents prepared according to a method comprising mixing an aqueous solution of a protein of interest with a solution comprising a surfactant in an alkane organic solvent in amounts and under conditions conducive to the formation of a reverse micelle solution, and evaporating the resulting reverse micelle solution to dryness, wherein the resulting protein composition is soluble in water miscible and water immiscible organic solvents.

15. The composition of claim 14 which comprises an anionic surfactant.

16. The composition of claim 15 which comprises AOT.

17. The composition of claim 10 in which the protein is an enzyme.

18. The composition of claim 14 in which the protein is an enzyme.

19. The composition of claim 10 which is at least about 90% soluble in an organic solvent.

20. The composition of claim 10 which is about 100% soluble in an organic solvent.

21. A composition comprising an organic solvent in which the protein composition of claim 10 has been dissolved.

22. The composition of claim 21 in which the protein is an enzyme.

23. The composition of claim 22 in which the organic solvent is a dry-cleaning solvent.

24. A method for producing a protein composition soluble in organic solvents, comprising mixing a solution of a protein of interest in an aqueous buffer with a solution comprising an anionic surfactant in a water immiscible organic solvent in amounts and under conditions conducive to the formation of a reverse micelle solution, and evaporating the resulting reverse micelle solution to dryness.

25. The method of claim 24 in which the surfactant is AOT and the solvent is an alkane.

26. The method of claim 25 in which the solvent is an octane.

27. The method of claim 26 in which the protein is an enzyme.

28. A method for producing a composition of a biologically active material soluble in organic solvents, comprising mixing a biologically active material not normally soluble in organic solvents with a solution comprising a surfactant in a water immiscible organic solvent in amounts and under conditions conducive to the formation of a reverse micelle solution, and evaporating the resulting reverse micelle solution to dryness.

29. A composition prepared according to the method of claim 28.

* * * * *